United States Patent [19]

Molina

[11] 4,002,905
[45] Jan. 11, 1977

[54] PENETRANT FLAW INSPECTION METHOD

[75] Inventor: Orlando G. Molina, Westminster, Calif.

[73] Assignee: Rockwell International Corporation, El Segundo, Calif.

[22] Filed: Feb. 23, 1976

[21] Appl. No.: 660,594

[52] U.S. Cl. .................................. 250/302; 73/104; 252/301.19
[51] Int. Cl.$^2$ ................. G01N 19/08; G01N 21/16; C09K 11/06
[58] Field of Search ..................... 73/104; 250/302; 252/301.19

[56] References Cited

UNITED STATES PATENTS

| | | | |
|---|---|---|---|
| 2,953,530 | 9/1960 | Switzer | 252/301.19 |
| 3,716,492 | 2/1973 | Graham et al. | 252/301.19 |
| R26,888 | 5/1970 | Alburger | 252/301.19 |

*Primary Examiner*—Richard C. Queisser
*Assistant Examiner*—John P. Beauchamp
*Attorney, Agent, or Firm*—C. T. Silberberg; L. Lee Humphries

[57] ABSTRACT

A water washable substantially biodegradable dye penetrant composition having excellent sensitivity and high stability, for use in non-destructive testing of objects to locate voids and defects therein, said composition consisting essentially of an organic dye, preferably a fluorescent dye, and a carrier or solvent for said dye, in the form of a mixture of certain ethoxylated linear alcohols, particularly a combination of biodegradable nonionic surfactants each comprised of ethoxylates of a mixture of secondary alcohols having linear alkyl chains of from 11 to 15 carbon atoms, one of which contains an average of 5 moles of ethylene oxide, and another of which contains an average of 9 moles of ethylene oxide. In the method of application of the dye penetrant compositions, such composition is applied to the surface of an object containing cracks and flaws, water is applied to the surface of the object to remove excess liquid dye penetrant composition from the surface without removing such penetrant from the cracks and defects, and with or without a developer, the surface of the object is viewed under suitable lighting conditions, e.g. ultraviolet or black light when the dye in the penetrant is a fluorescent dye, to locate any cracks or defects in the surface of the body as indicated by colored traces from the dye penetrant remaining in the cracks and flaws.

15 Claims, No Drawings

PENETRANT FLAW INSPECTION METHOD

BACKGROUND OF THE INVENTION

This invention relates to an improved dye penetrant composition and method for non-destructively testing material specimens to locate and identify surface voids, cracks or defects, and more particularly to an improved liquid vehicle for such a dye penetrant. The invention is especially concerned with a novel easily water washable, stable and sensitive dye penetrant composition of the above type having the characteristics of being able to disclose a wide range of defective conditions in parts, employing as solvent or vehicle essentially a biodegradable nonionic surfactant in the form of certain combinations or mixtures of certain ethoxylated alcohols; and to a method utilizing such dye penetrant composition for non-destructive testing of parts.

In known penetrant inspection methods for rapid location and evaluation of surface flaws or cracks in test bodies or parts, a dye penetrant composition, preferably containing a fluorescent dye, and which will penetrate the openings of the surface cracks or flaws in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions, such as invisible fluorescigenous light, and the location of the surface flaws is revealed by the emission of visible fluorescent light by the penetrant dye which was retained in the cracks or flaws after the penetrant composition was removed from the surface of the part.

For best efficiency, particularly for the detection and location of minute surface cracks and flaws, as well as intermediate size and gross cracks, it is necessary that the dye penetrant composition have high sensitivity.

Volatile type solvents are commonly employed for extending or thinning dye penetrant inspection solutions or compositions. This is done chiefly for the purpose of lowering the viscosity of the penetrant in order to adapt it for application in spraying systems. Thus for example solvents such as kerosene, light fuel oils, and methyl ethyl ketone, all highly volatile solvents, have heretofore been employed in prior art dye penetrants. See for example U.S. Pat. NO. 2,806,959. Further, most dye penetrant solutions in practice generally require the use of a combination of solvents, including primary and secondary solvents, extender solvents and wetting agents.

However, the use of volatile solvents in dye penetrant compositions has certain disadvantages. Thus, the use of volatile solvents in dye penetrants results in the evolution of fumes and solvent vapors which are rapidly formed by the evaporating solvent.

In addition, stability of the penetrant solution is essential without the necessity for carefully balancing the various liquid components of a dye penetrant solution in order to obtain efficient penetration of the solution into the cracks and flaws of a part, dye solubility, wetting action and washability control.

An additional criterion has recently developed also with respect to dye penetrant solutions and compositions. Generally, dye penetrant solutions presently being used and containing solvents and wetting agents present a disposal problem in that they are substantially non-biodegradable, that is, they are very difficult to decompose by bacteria in sewage disposal plants. Hence the necessity for the development of dye penetrant solutions and compositions which are biodegradable, that is which employ dye solvents and carriers which are biodegradable, and are readily available despite the petrochemical shortage, has attained considerable importance.

In my U.S. Pat. No. 3,915,886 there is disclosed a novel dye penetrant which has improved washability and sensitivity characteristics, and which is biodegradable, containing as the vehicle for the dye, certan biodegradable nonionic ethoxylated alcohols. Although dye penetrants of this type have been tested extensively and have proved highly satisfactory and effective for most applications, occasionally some undesirable fluorescent background was left on the parts undergoing inspection. Also, although high sensitivity formulations can be provided by means of the penetrant compositions of my above application, including the aforementioned nonionic ethoxylated alcohols as surfactant, in some instances an even greater sensitivity range is desired for the dye penetrant, especially when working with parts or specimen containing a wide range of cracks or defects of varying sizes. Also, it has been found that when employing many of the nonionic ethoxylated alcohols in dye penetrants according to my U.S. Pat. No. 3,915,886, it is necessary to employ relatively high volumes of water and increased pressure to wash excess penetrant from the surface of the test specimen.

Accordingly, an object of the present invention is the provision of a readily water washable dye penetrant solution or composition which avoids the use of the conventional primary and secondary volatile and nonvolatile solvents, and multiplicity of wetting agents, and their above-noted disadvantages, and which is highly stable, has excellent sensitivity and is essentially non-flammable and non-toxic. A particular object of the invention is to provide a dye penetrant solution of the above-noted type, having good wettability characteristics, and which employs a liquid carrier or vehicle for the dye, which is generally of the type disclosed in my U.S. Pat. No. 3,915,886, which is readily available and is biodegradable, thus rendering the dye penetrant solution essentially biodegradable, and which has certain additional advantages.

DESCRIPTION OF THE INVENTION

It has now been found that the above objects and advantages can be accomplished according to the invention, and an improved biodegradable dye penetrant composition provided, by employing as a solvent or carrier for the dye, e.g. fluorescent dye, in the dye penetrant, a combination of biodegradable nonionic surfactants comprised of certain ethoxylated linear alcohols, of the type disclosed in my U.S. Pat. No. 3,915,886, particularly a combination of such biodegradable nonionic surfactants, each preferably comprised of ethoxylates of a mixture of secondary alcohols having linear alkyl chains of from 11 to 15 carbon atoms, one of which surfactants contains an average of 5 moles of ethylene oxide, and another of which contains an average of 9 moles of ethylene oxide, such dye penetrant compositions being substantially free of odor and having an unusually high flash point in excess of 400° F. If desired, where a particularly high sensitivity material is required, a third member of such series of biodegradable nonionic surfactants can be incorporated, the latter surfactant also preferably comprised of ethoxylates of a mixture of secondary alcohols having linear alkyl chains of from 11 to 15 carbon atoms, and which contains an average of 3 moles of ethylene oxide.

By employment of a dye penetrant composition of the above type, utilizing a combination of the above nonionic ethoxylated alcohols containing 5 moles of ethylene oxide and 9 moles of ethylene oxide, respectively, it has been found that a substantial improvement is obtained, in the absence of fluorescent background remaining on the parts, permitting sharp and brilliant indications of defects on a non-fluorescent background, and permitting use of substantially reduced amounts of water for washing and reduced water pressure and time of washing, as compared to the use of for example the individual ethoxylated alcohols. In addition, the invention combination of biodegradable surfactants employed in the dye penetrant of the invention has the ability to detect and disclose a very wide range of defective conditions or cracks of varying sizes, usually only capable of being detected by employing several different levels of penetrant formulations of the prior art, that is penetrants which contain varying amounts of dye.

The dye penetrant composition of the present invention otherwise has substantially the same improved properties and advantages of the dye penetrant of my U.S. Pat. No. 3,915,886, in that it does not require the presence of any additional solvents or wetting agents, generally employed in prior art dye penetrant solutions and compositions. The dye penetrant solution of the invention is accordingly very simple to mix, and to use, is economical, and not only is biodegradable, but the above-noted nonionic solvent carrier for the dye is readily available since it is less dependent on petrochemical sources for its manufacture.

Thus, it has been found according to the present invention that the simple addition of a small amount of dye, preferably in proportions hereinafter disclosed, to the above-noted specific combination of nonionic ethoxylated alcohols results in an efficient powerful dye penetrant with highly unique and desirable characteristics including instant washability from the surface of parts without loss of dye penetrant solution entrapped within the defects and cracks. Such dye penetrant solution penetrates the cracks and flaws in the surface of parts instantly and without having to wait for relatively long periods for this purpose as in the case of many commercial penetrants. Thus, the invention provides a dye penetrant solution employing essentially a single type of biodegradable surfactant as carrier or vehicle for the dye, while at the same time obtaining high stability of the dye in the carrier, and also obtaining excellent wettability and instant washability of the dye penetrant solution from the part surface without dislodging the dye penetrant from the cracks and flaws in a part surface. Since the above-noted nonionic dye solvent or carrier employed has extremely low volatility it provides dye penetrant solutions of uniform and stable sensitivity, and which afford excellent crack and defect detection. Further, the nonionic solvent or carrier of the dye penetrant solution hereof has a high flash point, of the order of 400° F., and is essentially non-flammable, has low volatility, is substantially odorless, and of particular significance, it is biodegradable, thus conferring such properties on the dye penetrant solution.

The nonionic biodegradable solvent or carrier for the dye according to the invention consists of certain combinations of two or more surfactants of the same family, each consisting of ethoxylates of a mixture of linear secondary aliphatic alcohols, with the hydroxyl groups randomly distributed, the linear aliphatic hydrophobic portion of such alcohols being a mixture of alkyl chains containing in the range from 11 to 15 carbon atoms, one of such surfactants containing an average of 5 moles of ethylene oxide, and another of such surfactants containing 9 moles of ethylene oxide. If desired a third surfactant of the above same family can be incorporated, containing an average of 3 moles of ethylene oxide, for further enhanced sensitivity.

The above nonionic biodegradable surfactant combination employed as carrier for the dye penetrant of the invention is a combination or mixture of compounds or surfactants which can be represented by the formula:

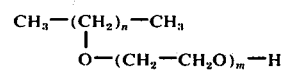

where n is in the range from 9 to 13, and m for one surfactant of the combination is 5 and for a second surfactant of the combination is 9, and which combination, if desired can also include a third surfactant as defined above, where m is 3.

Although preferably each of the above-defined surfactants of the combination is formed of a mixture of two or more linear alkyl hydrophobic chains ranging from $C_{11}$ to $C_{15}$, as noted below, the surfactant can contain a single such chain formed from a single secondary aliphatic alcohol of the types described below.

The linear alkyl hydrophobic portion of each of the above defined surfactants of the combination preferably is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of each of the surfactants of the combination is a poloxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a

group. Such hydrophilic polyoxyethylene chain is generally expressed in terms of an average number of moles of ethylene oxide.

Thus, the combination of biodegradable nonionic surfactants of the invention, and which are of the types defined in the above formula, preferably are those consisting of a mixture of ethoxylates of from 11 to 15 carbon atoms in the aliphatic hydrophobic chain, and containing an average of 5 and 9 moles of ethylene oxide, respectively, as the hydrophil, and which may also include an additional such surfactant containing 3 moles of ethylene oxide in the hydrophil.

Materials corresponding to these three biodegradable nonionic surfactants are marketed, respectively as:

| Tergitol | 15-S-3 |
| | 15-S-5 |
| | 15-S-9 |

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Thus, the basic combination or mixture of these materials in providing the dye penetrant of the invention, is a mixture of the above Tergitols 15-S-5 and 15-S-9. To this mixture there can be added optionally Tergitol 15-S-3.

The respective nonionic biodegradable surfactants employed as carrier or vehicle for the dye of the penetrant solution according to the invention, are prepared by reacting an alcohol or mixture of alcohols, as described above, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Any suitable dye generally employed in dye penetrant compositions can be incorporated into the combination of nonionic ethoxylated alcohol surfactants described above for producing the dye penetrant compositions of the invention. Preferably, however, a fluorescent dye is employed for this purpose. The ethoxylated surfactants vehicle for the dye is compatible therewith and has the ability to dissolve either small or relatively large amounts of the dye and to hold a high concentration of dye in solution while providing good resolution and clarity of the dye trace in the cracks and flaws. Thus, the amount of dye employed can be varied to change the sensitivity of the penetrant while maintaining the same washability, utilizing the combination of nonionic surfactants according to the invention.

As previously noted, the dye penetrant solution employed according to the invention preferably contains a fluorescent dye. Various types of fluorescent dyes can be employed including for example the dye marketed as Fluorol 7GA as well as other fluorescent dyes such as those marketed as Calcofluor Yellow, Azosol Brilliant Yellow 6GF, Rhodanine B, Rhodanine 6 GDN, Calcofluor White RW, Blancophor White AW, Auramine and Eosine G, and water soluble fluorescent dyes such as Blancophor FFG.

The dye penetrant composition employed according to the invention alternatively can contain non-fluorescent or daylight type dyes such as azo type dyes, e.g. syleneazo-beta-naphthol, Mefford No. 322 dye, believed to be o-toluene-axoxyleneazo-beta-naphthol, and the azo dyes marketed as Oil Red O and Sudan Red. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

The dye penetrant composition according to the present invention permits rapid and almost instantaneous removal or cleaning of the remaining dye penetrant from the object surface by water washing, e.g. by application of ordinary tap water, a water spray or a spray mixture of air and water, or by wiping with a water moistened cloth or a cloth moistened with a rapid drying solvent such as trichloroethane or alcohol, without any need for emulsifiers and the like. Thus, the dye penetrant composition hereof generally has excellent wettability and practically instantaneous washability with water without removing dye penetrant from the cracks and defects on the part surface.

However, if desired, small amounts of extenders such as kerosene, the iso-paraffinic materials marketed as "Isopar," and volatile solvents such as methyl ethyl ketone, isopropyl alcohol, and the like, and water, can be added to the dye penetrant composition of the invention containing the ethoxylated alcohol carrier, to vary the properties thereof. It is noted however that in preferred practice these additives are not employed and in effect a "one liquid" solution is provided according to the invention, in which the combination of the ethoxylated alcohol surfactants is essentially the sole carrier for the dye. Also, if desired, corrosion inhibitors such as, for example, morpholine, can be added in a small amount such as 0.01 to 0.1% by volume of the dye penetrant composition, particularly where the object being tested is highly susceptible to corrosion, such as magnesium.

The amount of dye which is incorporated into the ethoxylated alcohol surfactant combination or carrier to produce the dye penetrant composition of the invention, can range from about 0.1 to 15, preferably about 0.5 to about 10, parts of the dye, or mixtures thereof, per 100 parts of the total combination of ethoxylated alcohol surfactants by weight. In preparing the dye penetrant composition of the invention, the dye is simply added to the ethoxylated alcohol carrier combination in the desired proportion. The resulting dye penetrant composition has both high and low temperature stability.

Where a developer composition is employed, any one of the three general types of developer compositions, namely dry powder, wet aqueous (water-base) and wet non-aqueous (volatile solvent base) developer compositions can be employed. In each case, the developer composition contains a light colored powder, forming a coating which contrasts with the color of the dye in the penetrant and which acts as a wick or blotter, and causes liquid penetrant containing the dye, e.g. fluorescent dye, which was retained in the cracks or surface flaws, to be drawn up out of the surface defects by capillary action and to "bleed" through the powder. Preferred developer compositions for use in conjunction with the dye penetrant composition according to the invention, are those described in my U.S. Pat. No. 3,803,051, which is a dry powder developer containing fumed alumina, fumed silica, fumed titanium dioxide and talc, and in my U.S. Pat. No. 3,748,469, and which is a wet nonaqueous developer composition consisting essentially of isopropyl alcohol, talc and glycol monobutyl ether. The descriptions of such developer compositions contained in the above patents are incorporated herein by reference.

The ethoxylate surfactant containing 5 moles ethylene oxide, of the surfactant combination employed herein is generally employed in an amount of about 29 to about 90%, preferably about 49 to about 85%, and the amount of ethoxylate surfactant containing 9 moles of ethylene oxide generally in an amount of about 9 to 70%, preferably about 14 to about 50%, by weight of the penetrant composition. Usually a larger amount of the former surfactant containing 5 moles of ethylene oxide as compared to the latter surfactant containing 9 moles of ethylene oxide, is utilized. By increasing the amount of such surfactant containing 5 moles of ethylene oxide to the surfactant containing 9 moles of ethylene oxide, the sensitivity of the dye penetrant is increased. An increase in the amount of the latter surfactant with respect to the amount of the former tends to increase water washability, so that a proper balance of these two surfactants provides the desired sensitivity and washability properties.

With rough surfaces as in castings, smaller amounts of dye are employed in the surfactant combinations vehicle of the invention, for obtaining brilliant fluorescence from gross cracks. For parts with smooth surfaces, larger amounts of dye are used in the surfactant combination vehicle in order to obtain high fluorescent indications from minute cracks in such parts. Thus, the dye penetrant composition of the invention employing the above combination of biodegradable nonionic ethoxylated alcohol surfactants also can be tailored to have varying degrees of sensitivity for detection of the smallest microcracks to gross cracks in a part surface by generally varying the amount of dye incorporated. This is illustrated by the compositions I, II, III and IV in Table 1 below:

TABLE 1

| | COMPOSITIONS (parts by weight) | | | |
|---|---|---|---|---|
| | I | II | III | IV |
| | Sensitivity Level | | | |
| COMPONENTS | Super high | High | Medium | Low |
| Tergitol 15-S-5 | 75.0 | 75.0 | 75.0 | 75.0 |
| Tergitol 15-S-9 | 25.0 | 25.0 | 25.0 | 25.0 |
| Calcofluor White RW | 5.0 | 2.5 | 1.25 | 0.675 |
| Fluorol 7GA | 1.5 | 0.75 | 0.375 | 0.187 |
| TOTAL | 106.5 | 103.25 | 101.625 | 100.862 |

Composition I provides a very high sensitivity performance, and is particularly advantageous for inspection of parts having a very smooth surface with microcracks. The high sensitivity dye penetrant Composition II is also suitable for this purpose. The medium sensitivity Composition III is suitable for detection of cracks of intermediate size, and the low sensitivity dye penetrant Composition IV is employed for detection of gross cracks. It will be noted that the sensitivity of Compositions I to IV varies with the amount of dye present, the sensitivity generally increasing with increase in dye concentration.

It is noteworthy that although the amount of dye in Compositions I, II, III and IV varies, these compositions containing the combination of Tergitols 15-S-5 and 15-S-9, have essentially the same water washability characteristics when subjected to normal washing conditions using a water spray or a water-air spray. Moreover, under such normal washing conditions, and irrespective of dye concentration, the parts following such washing operation employing any of the above compositions I to IV are observed to be essentially free of fluorescent background so that the fluorescent indications of cracks and flaws are brilliant, with sharp contrast against the background metal of the part.

Representative examples of effective dye penetrant formulations provided by employing a combination of Tergitol 15-S-5 and Tergitol 15-S-9, in varying proportions, and which have varying sensitivity, are set forth in Table 2 below. In Table 2, the proportions are expressed in terms of parts by weight.

TABLE 2

| | COMPOSITIONS | | |
|---|---|---|---|
| | V | VI | VII |
| | Sensitivity Level | | |
| COMPONENTS | High | Medium | Low |
| Tergitol 15-S-5 | 65 | 50 | 35 |
| Tergitol 15-S-9 | 35 | 50 | 65 |
| Calcofluor White RW | 5.0 | 5.0 | 5.0 |
| Fluorol 7GA | 1.5 | 1.5 | 1.5 |

From Table 2 above, it is seen that the sensitivity of the respective formulations is increased by increasing the amount of Tergitol 15-S-5 employed in the respective formulations in combination with Tergitol 15-S-9, the amount of dye remaining constant.

Although ethoxylates as defined above, having 3 moles of ethylene oxide, as represented by Tergitol 15-S-3, are essentially water insoluble, this material optionally can be incorporated in the above combination or mixture of Tergitol 15-S-5 and Tergitol 15-S-9 in the dye penetrant composition according to the invention. The amount of such ethoxylate containing 3 moles of ethylene oxide which can be employed can range from 0 to about 25% by weight of the penetrant formulation. Although Tergitol 15-S-3 tends to reduce somewhat the water washability of the resultant dye penetrant, such surfactant is preferably employed in relatively small amount as noted above, so as not to affect water washability in any significant degree, while increasing the sensitivity of the penetrant.

Representative examples of the above dye penetrant compositions containing a combination of three of the above-noted ethoxylates in admixture are set forth in Table 3 below; the amounts being expressed as parts by weight.

TABLE 3

| COMPONENTS | COMPOSITIONS VIII | IX | X |
|---|---|---|---|
| Tergitol 15-S-5 | 75 | 60 | 50 |
| Tergitol 15-S-9 | 20 | 25 | 30 |
| Tergitol 15-S-3 | 5 | 15 | 20 |
| Calcofluor White RW | 5 | 5 | 5 |
| Fluorol 7GA | 1.5 | 1.5 | 1.5 |

The following examples serve to illustrate but are not limitative of the benefits and advantages obtained by practice of the present invention.

EXAMPLE 1

The fluorescent dye penetrant Composition I above was applied as by spraying, to one-half of the surface of a chromium-plated brass test panel containing minute cracks of the order of 0.00002 to 0.0001 inch in width, closely distributed over its entire surface. A water wash was then applied as by an air-water spray over the coating of the dye penetrant Composition I on the test panel, washing away the dye penetrant on the surface of the panel without dislodging the dye penetrant from the surface cracks and thus entrapping the penetrant therein.

The other half of the test panel surface was sprayed with fluorescent dye penetrant solution similar to Composition I, and containing the same dyes and amounts thereof but containing only Tergitol 15-S-5 in an amount of 100 parts by weight, and designated Composition I', followed by application of an air-water spray to the surface of the panel to remove excess dye penetrant from the surface of the panel.

It was noted that substantially smaller amounts of wash water and at about one half the pressure was required for washing employing the invention Composition I containing the combination of ethoxylate surfactants as compared to Composition I' containing the single ethoxylate surfactant, and the time for washing using Composition I was reduced to less than half as compared to the amount of time when employing Composition I'.

Both halves of the test panel surface to which penetrant Composition I above and the Composition I' penetrant were initially respectively applied, were then covered with a powder developer having the following composition, according to my above U.S. Pat. No. 3,803,051.

| COMPONENTS | Per Cent by Weight |
|---|---|
| Talc | 52 |
| Alumina | 35 |
| Silica | 4 |
| TiO$_2$ | 9 |

The above developer was permitted to dwell over the two half surfaces of the test panel for a period of about 2 minutes.

Excess developer composition was then carefully removed from both half surfaces of the test panel by means of a gentle air blast.

The panel was then placed under black light (fluorescent) illumination and the respective half surfaces viewed in such illumination. It was observed that the first half side of the panel which had initially been treated with dye penetrant Composition I of the present invention, disclosed fluorescent indications from numerous readily defined microcracks therein, such fluorescent indications being sharper and more brilliant than the fluorescent indications from the microcracks on the half side of the panel which had been initially treated with the dye penetrant containing only Tergitol 15-S-5, as result of some slight fluorescent background remaining on the latter half side of the panel.

EXAMPLE 2

Dye penetrant inspection tests were carried out in a manner generally similar to the procedure of Example 1, employing Composition II on a test panel similar to that of Example 1, Composition II on a test panel containing cracks of intermediate size, and employing Composition IV on a test panel having gross cracks.

In each of the three tests above, bright fluorescent indications were obtained from the cracks of fine size on the first panel, from the cracks of intermediate size on the second panel, and from the gross cracks on the third panel, employing Compositions II, III and IV, respectively comparable to the brightness and sensitivity of the fluorescent indications obtained employing Composition I in Example 1, again free of any residual background fluorescence.

From Examples 1 and 2 above, it was observed that Compositions I and II function as super high to high sensitivity dye penetrant formulations for detecting microcracks, dye penetrant Composition III functions as a medium sensitivity dye penetrant for detecting intermediate size cracks, and dye penetrant Composition IV functions as a low sensitivity dye penetrant for detecting gross cracks, employing the combination of surfactants Tergitols 15-S-5 and 15-S-9 according to the invention. Thus there is provided according to the invention a dye penetrant composition having excellent sensitivity and which can be tailored for a large sensitivity range necessary to detect from the most minute microcrack to the largest gross crack, without requiring any change in the washability of the formulation. In other words, Compositions I, II, III and IV above all have the same improved washability characteristics when adequate amounts of water are used for washing, despite the differences in dye concentration of these respective compositions. Thus, it is believed that the dye penetrant of the invention employing the above defined combination of ethoxylated alcohol surfactants as carrier has the unique property of great affinity for remaining within the cracks and defects of a part, while that portion of the dye penetrant contacting the surface of the parts containing the cracks, can be almost instantaneously washed away with simple water spraying using adequate amounts of water, without dislodging the penetrant entrapments.

In addition, the washability properties of the dye penetrant of the invention containing a combination of the defined ethoxylated surfactants are superior to those of the dye penetrants of my above copending application, containing a single ethoxylated surfactant, resulting in more efficient and complete removal of any residual background fluorescence.

EXAMPLE 3

Tests on aluminum panels having a very smooth surface and containing microcracks of the order of 0.00002 to 0.0001 inch in width, were carried out employing a procedure similar to that employed in Example 1, utilizing Composition V containing a combination of Tergitol 15-S-5 and Tergitol 15-S-9, in a ratio of 65 to 35 parts by weight, respectively.

Results obtained were similar to those obtained in Example 1, but the test panel to which Composition V was applied required a slightly more rigorous water wash due to the presence of Tergitol 15-S-3 than in the case of the test panel containing Composition I in Example 1.

EXAMPLE 4

The procedure of Example 1 was essentially followed, but employing in place of Composition I, a non-fluorescent water washable biodegradable dye penetrant solution according to the invention, consisting of 12 parts of Tergitol 15-S-5, 4 parts of Tergitol 15-S-9 and 1 part of Oil Red O dye, by volume, applied over the entire surface of the test panel.

Excellent results of crack detectability were obtained employing such biodegradable non-fluorescent dye penetrants.

However, the brightness and sensitivity of the colored dye traces obtained employing the biodegradable non-fluorescent dye penetrant of this example were not as great as for the fluorescent biodegradable dye penetrant Composition I in Example 1

EXAMPLE 5

The procedure of Example 1 was followed except that in place of the powder developer employed in Example 1, a nonaqueous developer having the following composition, according to my above U.S. Pat. No. 3,748,469 was employed:

| COMPONENTS | Per Cent By Weight |
|---|---|
| Isopropyl alcohol | 70.5 |
| Talc | 28.6 |
| Glycol monobutyl ether | 0.9 |

The above developer was permitted to remain on the panel surfaces to which it was applied for a period of 2 minutes, until substantially all of the isopropyl alcohol had evaporated and a substantially dry powder coating was formed.

Results similar to the results of Example 1 were obtained.

EXAMPLE 6

Test procedure similar to Example 1 was followed but employing dye penetrant Composition VIII of Table 3, containing a combination of Tergitols 15-S-5, 15-S-9 and 15-S-3.

Results obtained were similar to those obtained employing Composition I in Example 1, it being noted that dye penetrant Composition VIII produced somewhat reduced water washability of excess penetrant from the panel surface, while affording somewhat higher sensitivity in permitting detection of the minute cracks in the panel with somewhat more brilliant indications than in the case of Composition I, containing the combination of only the two surfactants 15-S-5 and 15-S-9.

EXAMPLE 7

Test procedure similar to that of Example 1 was carried out employing each of the respective Compositions I, II, III and IV in an automatic conveyorized penetrant system for processing various parts and specimens.

Good washability was obtained on all parts using a short relatively constant washing time on each of the respective parts for each of the above compositions, regardless of crack size, with excellent sensitivity of the resulting fluorescent indications in each case.

On the other hand, various prior art formulations could not be employed for such automatic processing since each such formulation requires a different and independent washing time due to differences in washability for each such formulation for different size cracks in parts.

From the foregoing, it is seen that the invention provides a highly effective substantially biodegradable water washable dye penetrant composition employing a dye carrier or vehicle in the form of certain combinations of ethoxylated alcohols, which permits substantially instantaneous removal of dye penetrant from the surface of the part in a single wash operation, while maintaining the dye penetrant in the cracks or defects of the part, followed by further processing as desired in the conventional manner for viewing under suitable e.g. fluorescent, lighting conditions, to obtain improved brilliance, definition and resolution of dye traces from cracks and flaws in the part surface, as compared to prior art penetrants, and affording a substantially non-flammable high performance dye penetrant composition having a wide range of sensitivity with improved washability characteristics, which results in a surface substantially free of undesirable fluorescent background, especially in rough metallic surfaces, and avoiding the use of volatile extenders and thinners in the dye penetrant, and which has high flash point, low flammability and volatility, is nontoxic and essentially odorless, and of particular importance is biodegradable. The improved dye penetrant of the invention is quick acting and rapidly penetrates surface defects of parts, and the combination of surfactants employed in the dye penetrant aids in providing brilliant indications without requiring high dye concentrations.

Since various changes and modifications of the invention will occur to and can be made readily by those skilled in the art without departing from the invention concept, the invention is not to be taken as limited except by the scope of the appended claims.

I claim:

1. A method for detecting cracks and flaws in the surface of an object, which comprises applying to said surface a water washable biodegradable liquid dye penetrant composition which comprises (1) a major amount of a combination of biodegradable nonionic surfactants consisting of ethoxylates of linear secondary aliphatic alcohols, with the hydroxyl groups randomly distributed, the linear aliphatic portion of said alcohols being alkyl chains containing in the range from 11 to 15 carbon atoms, one of said biodegradable surfactants containing an average of 5 moles of ethylene oxide and another of said biodegradable surfactants containing an average of 9 moles of ethylene oxide, and (2) a small amount of a dye soluble in said combination of biodegradable surfactants, removing said dye penetrant composition from said surface without removing said dye penetrant composition from said cracks and flaws in said surface, and viewing the surface of said object under lighting conditions to obtain colored traces from the dye in said cracks and flaws.

2. A method as defined in claim 1, said liquid dye penetrant composition consisting essentially of said combination of nonionic surfactants as the sole liquid carrier for said dye.

3. A method as defined in claim 1, said removal of said dye penetrant composition being carried out by application of a water wash over said surface.

4. A method as defined in claim 3, said water wash being carried out by spraying water over said surface.

5. A method as defined in claim 1, wherein said dye is a fluorescent dye and said surface of said object is viewed under fluorescigenous light to obtain colored fluorescent traces from the dye in said cracks and flaws, substantially free of any fluorescent background.

6. A method as defined in claim 1, including applying a developer to said surface after removing said dye penetrant composition from said surface and prior to said viewing the surface of said object.

7. A method as defined in claim 1, wherein said ethoxylates of said alcohols forming said surfactants have the formula:

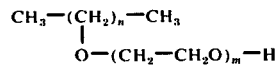

where n is in the range from 9 to 13, m for said one of said surfactants being 5 and m for said another of said surfactants being 9, and said dye is present in said composition in an amount ranging from about 0.1 to 15 parts per 100 parts, by weight of the total combination of said surfactants.

8. A method as defined in claim 1, wherein the linear alkyl hydrophobic portion of each of said surfactants is a mixture of $C_{11}$ to $C_{15}$ linear chains, and the hydrophilic portion of each of said surfactants is a polyoxyethylene chain randomly attached to the linear alkyl hydrophobic chains through an ether linkage; and said dye is present in said composition in an amount ranging from about 0.1 to 15 parts, per 100 parts, by weight of the total combination of said surfactants.

9. A method as defined in claim 8, the amount of said one of said ethoxylated surfactants containing 5 moles of ethylene oxide being about 29 to about 90%, and the amount of said another ethoxylated surfactant containing 9 moles of ethylene oxide being about 9 to about 70%, by weight of said dye penetrant composition.

10. A method as defined in claim 8, said combination of nonionic surfactants including a third said nonionic surfactant, said third surfactant containing an average of 3 moles of ethylene oxide.

11. A method as defined in claim 9, said combination of nonionic surfactants including a third said nonionic surfactant, said third surfactant containing an average of 3 moles of ethylene oxide, and employed in an amount of 0 to about 25%, by weight of said dye penetrant composition.

12. A method as defined in claim 7, wherein said dye is a fluorescent dye and said surface of said object is viewed under fluorescigenous light to obtain colored fluorescent traces from the dye in said cracks and flaws, substantially free of any fluorescent background.

13. A method as defined in claim 9, wherein said dye is a fluorescent dye and said surface of said object is viewed under fluorescigenous light to obtain colored fluorescent traces from the dye in said cracks and flaws, substantially free of any fluorescent background.

14. A method as defined in claim 13, said removal of said penetrant composition being carried out by application of a water wash over said surface.

15. A method as defined in claim 6 said developer being a dry powder, aqueous or non-aqueous developer.

* * * * *